United States Patent
Ing

(10) Patent No.: US 8,692,810 B2
(45) Date of Patent: Apr. 8, 2014

(54) METHOD FOR DETERMINING THE LOCATION OF IMPACTS BY ACOUSTIC IMAGING

(75) Inventor: Ros Kiri Ing, Paris (FR)

(73) Assignee: Elo Touch Solutions, Inc., Milpitas, CA (US)

( * ) Notice: Subject to any disclaimer, the term of this patent is extended or adjusted under 35 U.S.C. 154(b) by 1355 days.

(21) Appl. No.: 11/911,398

(22) PCT Filed: Apr. 13, 2005

(86) PCT No.: PCT/EP2005/005207
§ 371 (c)(1),
(2), (4) Date: Oct. 12, 2007

(87) PCT Pub. No.: WO2006/108443
PCT Pub. Date: Oct. 19, 2006

(65) Prior Publication Data
US 2009/0122028 A1 May 14, 2009

(51) Int. Cl.
*G06F 3/043* (2006.01)

(52) U.S. Cl.
USPC .......................... 345/177; 345/173; 367/118

(58) Field of Classification Search
USPC ............ 345/173, 177; 367/21, 38, 39, 41, 42, 367/118
See application file for complete search history.

(56) References Cited

U.S. PATENT DOCUMENTS

| | | | | |
|---|---|---|---|---|
| 6,723,929 B2 * | 4/2004 | Kent | ........................ | 178/18.04 |
| 6,871,149 B2 * | 3/2005 | Sullivan et al. | ................ | 702/56 |
| 7,184,898 B2 * | 2/2007 | Sullivan et al. | ................ | 702/56 |
| 7,345,677 B2 * | 3/2008 | Ing et al. | ...................... | 345/173 |
| 7,376,523 B2 * | 5/2008 | Sullivan et al. | ................ | 702/56 |
| 7,411,581 B2 * | 8/2008 | Hardie-Bick | ................. | 345/173 |
| 7,499,039 B2 * | 3/2009 | Roberts | ......................... | 345/177 |
| 7,511,711 B2 * | 3/2009 | Ing et al. | ....................... | 345/424 |
| 7,515,138 B2 * | 4/2009 | Sullivan | ........................ | 345/173 |
| 7,649,807 B2 * | 1/2010 | Ing | ................................ | 367/118 |
| 8,013,846 B2 * | 9/2011 | Bayramoglu et al. | ........ | 345/177 |
| 8,274,480 B2 * | 9/2012 | Sullivan | ........................ | 345/173 |
| 2001/0006006 A1 | 7/2001 | Hill | | |
| 2003/0066692 A1 * | 4/2003 | Devige et al. | ............. | 178/18.04 |
| 2004/0133366 A1 | 7/2004 | Sullivan et al. | | |
| 2004/0173389 A1 * | 9/2004 | Sullivan | ..................... | 178/18.04 |
| 2005/0083313 A1 * | 4/2005 | Hardie-Bick | ................. | 345/177 |
| 2005/0146511 A1 * | 7/2005 | Hill et al. | ....................... | 345/173 |
| 2005/0146513 A1 * | 7/2005 | Hill et al. | ....................... | 345/173 |
| 2005/0174338 A1 | 8/2005 | Ing et al. | | |
| 2005/0212777 A1 | 9/2005 | Ing et al. | | |
| 2006/0132464 A1 * | 6/2006 | Sullivan | ........................ | 345/173 |

FOREIGN PATENT DOCUMENTS

WO 03/107261 12/2003

OTHER PUBLICATIONS

International Search Report for PCT Application No. PCT/EP2005/005207 mailed on Dec. 14, 2005, 3 pages.
Wilcox P.D. et al. "A Signal Processing Technique to Remove the Effect of Dispersion From Guided Wave Signals," 7th Annual Review of Progress in Quantitative Nondestructive Evaluation Jul. 16-21, 2000, Ames, IA, USA, No. 557A, 2001, pp. 555-562, XP009058387 AIP Conference Proceedings AIP USA ISSN: 0094-243X.

* cited by examiner

*Primary Examiner* — Jason Mandeville
(74) *Attorney, Agent, or Firm* — Alston & Bird LLP

(57) ABSTRACT

A method for determining the location of an impact on a surface (1) comprising N acoustic sensors (2a, 2b, 2c), transmitting a sensed signal $s_i(t)$ to a processing unit (4) comprises the following steps (a) computing P intercorrelation products (b) calculating P inverse Fourier transforms $p'_{ij}(u)$ (c) computing for each area k, $P_k(u)=\Sigma P'_{ij}(u-\tau_{ijk})$; d) finding $k_0$, where a characterizing value of $P_{k0}(u)$ is greater than a given threshold value.

18 Claims, 3 Drawing Sheets

METHOD FOR DETERMINING THE LOCATION OF IMPACTS BY ACOUSTIC IMAGING

CROSS-REFERENCE TO RELATED APPLICATIONS

This application is being filed as a U.S. National Stage under 35 U.S.C. 371 of International Application No. PCT/EP2005/005207, filed on Apr. 13, 2005, the contents of which is hereby incorporated by reference in its entirety.

FIELD OF THE INVENTION

The present invention relates to a method for determining the location of impacts on an object and a device using this method.

BACKGROUND OF THE INVENTION

A known method for determining the location of impacts on an object is based on acoustic image generation. According to this method, a surface of the object is subdivided in M areas, for example like an array, and N acoustic sensors are fixed for example on the surface. Each acoustic sensor i is arranged to receive an acoustic signal generated from an impact on the object surface and to transmit a sensed signal $s_i(t)$ to a processing unit.

Figure 1A:
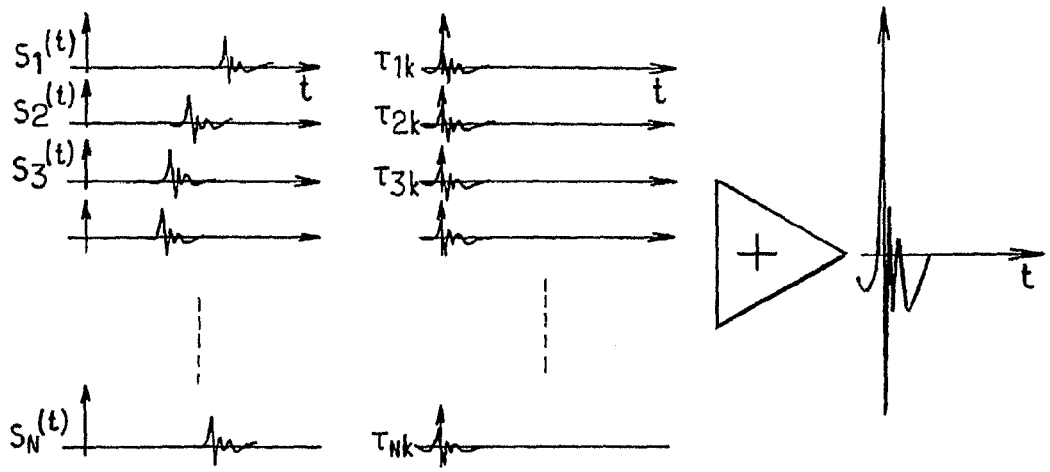
Figure 1B:
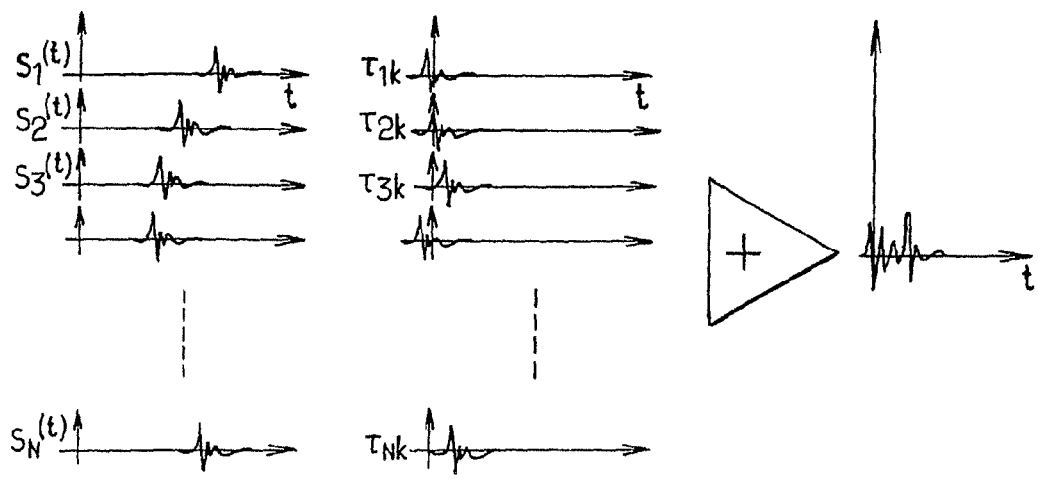

For each area k of the array, the sensed signals $s_i(t)$ are delayed of a time delay compensation $\tau_{ik}$ and summed forming $P_k$. This time delay compensation $\tau_{ik}$ is a determined value based on the respective locations of the area k and of the sensor i. As shown in FIG. 1a, if the sensed signals $s_i(t)$ are correctly delayed, i.e. if the impact was generated in the area k, the delayed signals are in phase and $P_k$ has an impulse shape. As opposed to and as shown in FIG. 1b, if the sensed signals $s_i(t)$ are not correctly delayed, i.e. if the impact was not generated in the area k, $P_k$ is wide and his maximal value is low. Thus, for each area k of the array, the $P_k$ maxima are computed, forming thus an acoustic image of the impact. A comparison of the $P_k$ permits then to localize an impact generated on the surface.

Yet, the time origin in such a method is not correctly determined, leading to synchronization problems in the processing unit. In consequence, failures to determine the location of impacts occur. Moreover, the accuracy of this method is dependant on the shape and, in particular, the duration of the impact signals. Then, the longer an impact signal lasts, the lower the accuracy is.

An object of the present invention is to provide a method for determining the location of an impact, whose accuracy does not depend on the impact signal waveform.

Another object of the invention is to provide a robust method for determining the location of impacts.

SUMMARY OF THE INVENTION

The invention thus proposes a method for determining the location of an impact on a surface of an object, said surface comprising N acoustic sensors, where N is at least 3, and M determined areas, said impact generating an acoustic signal, each sensor i receiving said acoustic signal and transmitting a sensed signal $s_i(t)$ to a processing unit, said method comprising the following steps:

(a) computing P intercorrelation products $P_{ij}(\omega) = S_i(\omega) \cdot S_j^*(\omega)$ where $S_i(\omega)$ is a Fourier transform of the sensed signal $s_i(t)$ sensed by the sensor i;

$S_j(\omega)$ is a Fourier transform of the sensed signal $s_j(t)$ sensed by the sensor j; and

* is the complex conjugate operator;

(b) calculating P inverse Fourier transforms $p'_{ij}(u)$ of said $P_{ij}(\omega)$;

(c) computing for each area k, $P_k(u) = \Sigma p'_{ij}(u - \tau_{ijk})$ and a characterizing value of $P_k(u)$, where $\tau_{ijk}$ is a determined value based on the respective locations of the area k and of the sensors i and j;

d) finding $k_0$, where the characterizing value of $P_{k_0}(u)$ is greater than the corresponding characterizing values of $P_k(u)$ for $k \neq k_0$.

In various embodiments of the method according to the invention, at least one of the following characteristics may be used:

the inverse Fourier transforms $p'_{ij}(u)$ equal $$p'_{ij}(u) = \int_{-\infty}^{+\infty} P_{ij}(m(\Omega)) \cdot \left(\frac{dm(\Omega)}{d\Omega}\right)^2 \cdot e^{j\Omega u} \cdot d\Omega$$

where $\Omega$ is a wavenumber coefficient; and where $m(\Omega)$ is a frequency corresponding to the wavenumber coefficient $\Omega$, according to a material dispersion relation;

u is a distance and $\tau_{ijk}$ is a length depending on the distance between the area k and the sensor i and the distance between the area k and the sensor j;

the material dispersion relation substantially equals $\Omega = \alpha \sqrt{\omega}$, where $\alpha$ is a coefficient depending on the object;

the material dispersion relation substantially equals $\Omega = \alpha \omega$, where $\alpha$ is a coefficient depending on the object;

the coefficient $\alpha$ depends on $\theta_{ik}$, where $\theta_{ik}$ is a determined angular value based on the respective locations of the area k and the sensor i;

the coefficient $\alpha$ depends on the temperature of the object $\alpha(T)$, where T is a temperature value;

the method further comprises an initializing mode comprising a step of determining the material dispersion relation of the object;

said step of determining the material dispersion relation includes the following sub-step of generating NSO impacts at determined locations;

said NSO impacts are generated at determined locations along a line linking two of the N sensors and equally spaced;

the step of determining the material dispersion relation further comprises the following sub-steps:

computing $p'_{ij}(u)$ with $\alpha$ test values;

for each $\alpha$ test value, computing $P_m(u) = \Sigma p'_{ij}(u - \tau_{ijm})$ for each impact m, and for each $\alpha$ test value, summing all the $P_m(u)$;

selecting $\alpha_{opt}$ which provides the greatest maximal value of the sums $\Sigma P_m(u)$;

the method further comprises an initializing mode comprising a step of determining the location of the N sensors on the surface;

the number of intercorrelation products $P_{ij}(\omega)$ equals $$P = \frac{N(N-1)}{2};$$

the characterizing value of $P_k(u)$ is one of the following parameters:
a maximal value of $P_k(u)$
a power of $P_k(u)$, or maximal square amplitude;
a maximal peak-to-peak amplitude;
a root mean square of $P_k(u)$; or
an energy of $P_k(u)$, which equals $$\int_{u_{min}}^{u_{max}} P_k^2(u) \cdot du.$$

a width pulse parameter of $P_k(u)$, which equals $$\int_0^{w_{max}} \text{REAL}\left(\int_{u_{min}}^{u_{max}} P_k(u)e^{juw} \cdot du\right),$$

where REAL (x) is the real part of the complex number x;
it is concluded that the impact occurred in the area $k_0$ only if the characterizing value of $P_{k_0}(u)$ is greater than a predetermined threshold of confidence;
it is concluded that the impact occurred in the area $k_0$ only if a contrast value defined by the ratio $f(P_{k_0}(u))/\text{MEAN}(f(P_{k,k\neq k_0}(u)))$ is greater than a predetermined threshold of confidence where MEAN is an averaging operator;
$P_{ij}(\omega)$ is normalized.

Another object of the invention is a device for determining the location of an impact on a surface of an object, said surface comprising M determined areas and said impact generating an acoustic signal, said device comprising:
a processing unit;
N acoustic sensors adapted to be borne by said surface, where N is at least 3, each sensor i receiving said acoustic signal and transmitting a sensed signal $s_i(t)$ to the processing unit,
wherein said processing unit comprises:
(a) means for computing P intercorrelation products
$P_{ij}(\omega)=S_i(\omega)\cdot S_j^*(\omega)$ where
$S_i(\omega)$ is a Fourier transform of the sensed signal $s_i(t)$ sensed by the sensor i;
$S_j(\omega)$ is a Fourier transform of the sensed signal $s_j(t)$ sensed by the sensor j; and
* is the complex conjugate operator;
(b) means for calculating P inverse Fourier transforms $p'_{ij}(u)$ of said $P_{ij}(\omega)$
(c) means for computing for each area k, $P_k(u)=\Sigma p'_{ij}(u-\tau_{ijk})$ and a characterizing value of $P_k(u)$, where $\tau_{ijk}$ is a determined value based on the respective locations of the area k and of the sensors i and j;
d) means for determining $k_0$, where the characterizing value of $P_{k_0}(u)$ is greater than the corresponding characterizing values of $P_k(u)$ for $k\neq k_0$.

Thus, by using intercorrelation products of the sensed signals, it is not required to determine the time origin for processing the signals. Consequently, there is no need of an accurate synchronization of the acoustic sensors to realize this invention. Moreover, as it will be explained, the phase of the intercorrelation product $P_{ij}(\omega)$ does not depend of the impact waveform. Thus, the waveform of the impact does not modify the accuracy of this method.

BRIEF DESCRIPTION THE DRAWINGS

Figure 2:
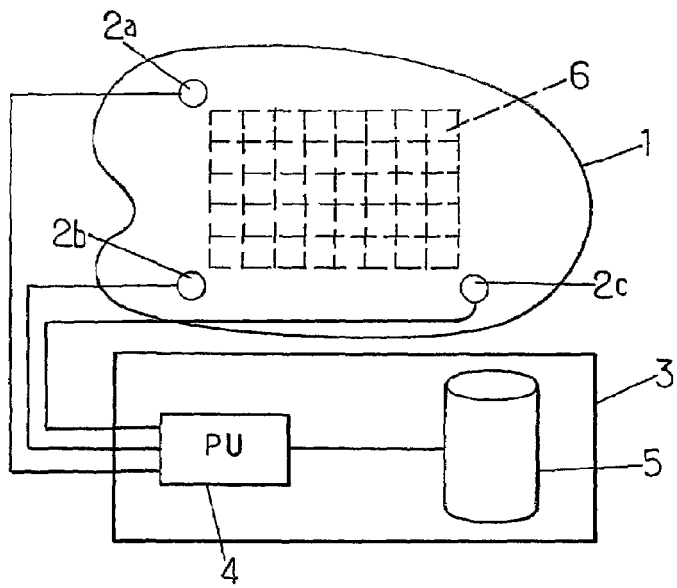
Figure 3:
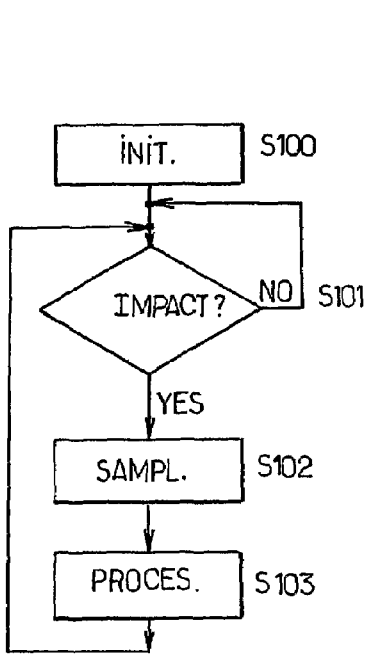
Figure 4:
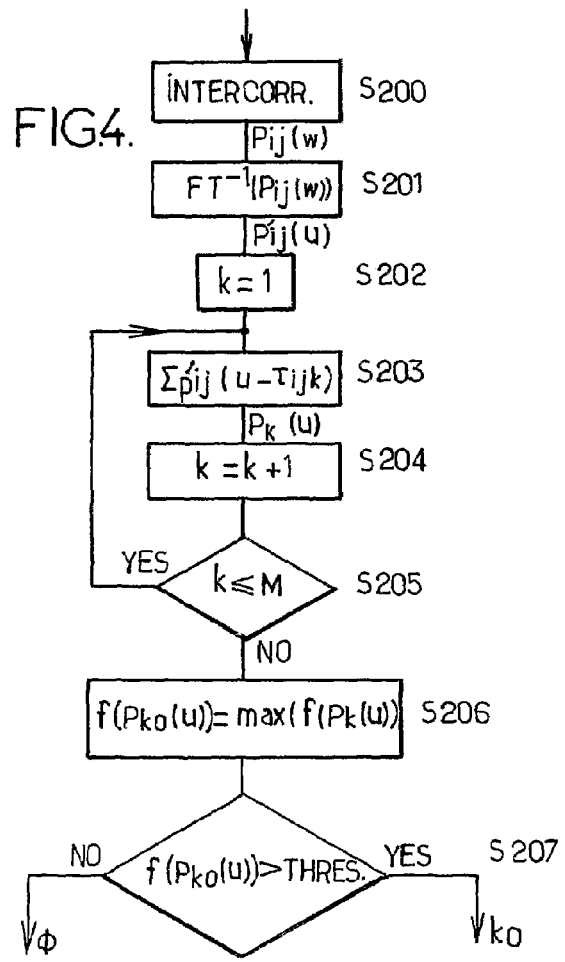
Figure 5:
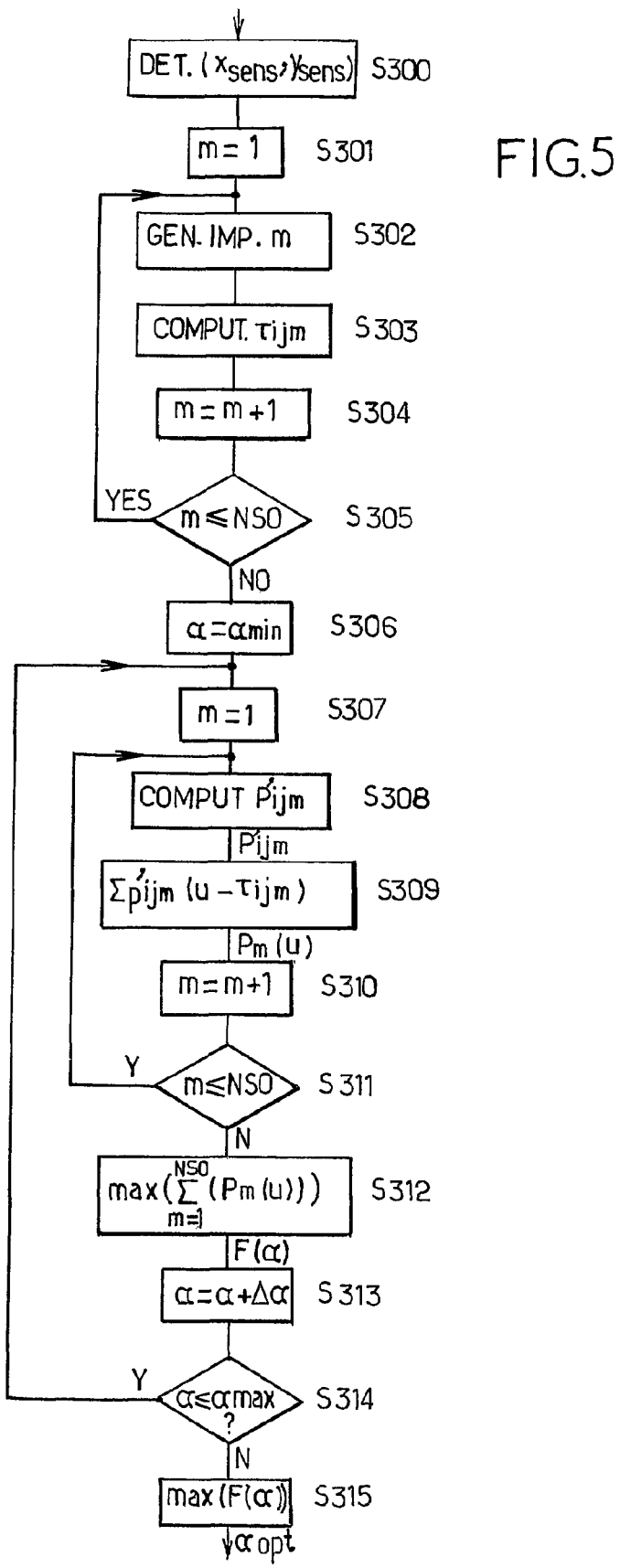

FIGS. 1a and 1b, already described, are chronograms illustrating an acoustic image formation according to the state of the art;

FIG. 2 is schematic of a device according to the invention;
FIG. 3 is a flowchart showing general operation of the device of FIG. 2;
FIG. 4 is a flowchart showing the operation during the processing step of the flowchart of FIG. 3;
FIG. 5 is a flowchart showing the operation during the initialization step.

DESCRIPTION OF PREFERRED EMBODIMENTS

As depicted in FIG. 2, a device 3 for determining the location of impacts according to the invention comprises N acoustic sensors, at least 3 like the depicted sensors 2a, 2b, 2c. It may further comprise a processing unit 4 connected to the acoustic sensors and a memory device, RAM for variables and ROM for code program and constant data, which is connected to the processing unit. Moreover, the acoustic sensors are fixed, for instance, on a surface 1 of an object. The surface 1 may be subdivided in M sensitive areas 6.

Before operation, as shown in FIG. 3, an initializing mode S100 (INIT.) is executed. This initializing mode will be described later. At step S101, a signal test (IMPACT?) is used for detecting an impact. For example, if a signal sensed by a sensor exceeds a determined threshold, the sensed signals $s_i(t)$ transmitted by the N sensors are sampled and saved in the processing unit 4 during step S102 (SAMPL.). Then, the processing step S103 (PROCES.) is executed.

As shown with more details in FIG. 4, the processing step begins with intercorrelation product calculations (INTERCORR.) at step S200. In fact, P independent intercorrelation products are carried out. Here, P equals the sum of the N−1 first integers, i.e.

$$P = \frac{N(N-1)}{2}$$

where N is the number of sensors. Each intercorrelation product $P_{ij}(\omega)$ equals
$P_{ij}(\omega)=S_i(\omega)\cdot S_j^*(\omega)$ where $S_i(\omega)$ is a Fourier transform of the sensed signal $s_i(t)$ sensed by the sensor i, $S_j(\omega)$ is a Fourier transform of the sensed signal $s_j(t)$ sensed by the sensor j, and * is the complex conjugate operator. The Fourier transforms are for instance Fast Fourier Transforms (FFT) which requires low calculation power. According to an embodiment, the intercorrelation products are normalized like for example in energy.

This intercorrelation product $P_{ij}(\omega)$ does not depend crucially on the time origin and on the impact waveform. Indeed, if we consider that $S_i(\omega)=C_i(\omega)\cdot\exp(-jkd_i)\cdot E(\omega)$
where $C_i$ is the frequency complex response of the sensor i, $d_i$ is the distance between the impact location and the sensor i, E impact waveform Fourier Transform. In this example, the wavenumber $k=\omega/C$, where C is the acoustic propagation velocity. Then, the intercorrelation product equals $P_{ij}(\omega)=S_i(\omega)\cdot S_j^*(\omega)$ or, $P_{ij}(\omega)=C_i(\omega)\cdot C_j^*(\omega)\cdot e^{(-jk(d_i-d_j))}\cdot E^*(\omega)$ As $E(\omega)\cdot E^*(\omega)$ is real, the time intercorrelation product $p_{ij}(t)$ depends mainly on the sensors response. A large sensors response bandwidth permits then to obtain really short impulses, in the limit of course of impact excitation frequency bandwidth. In this example, the sensors bandwidth is substantially [100 Hz, 7 kHz]. Moreover, if the intercorrelation product is normalized, it is not dependant on the amplitude of the sensed signal, and then of the impact intensity.

Then, in step S201, inverse Fourier transforms of the $P_{ij}(\omega)$ are computed. According to a first embodiment, the object material is non dispersive. This means that the wave propagation velocity of an acoustic signal does not depend on the frequency of this signal. In consequence, the waveform of a sensed signal propagated in this material is substantially equals to the original signal delayed of a delay which is a function of the material velocity and the distance between the source and the sensor. In this case, the inverse Fourier transform may be a usual inverse Fourier Transform or an inverse Fast Fourier Transform.

At step S202, k is initialized to 1 in order to carry out thereafter the computation of the sum $P_k(u)=\Sigma p'_{ij}(u-\tau_{ijk})$ (S203) for each area k of the surface, where $p'_{ij}(u)$ is the inverse Fourier transform of $P_{ij}(\omega)$. In the current case of non dispersive material, $\tau_{ijk}$ are delays based on the difference between respectively the distance from the area k to the sensor i and the distance from the area k to the sensor j. These values may be stored for instance in the memory means 5 of the device 1. They may be computed in the initializing mode S100 by the operator or determined during the design of this device.

Thus, if the impact was generated in the area k, all the $p'_{ij}(u-\tau_{ijk})$ are in phase, and $P_k(u)=\Sigma p'_{ij}(u-\tau_{ijk})$ will substantially be an impulse. On the contrary, if the impact was not generated in the area k, $P_k(u)=\Sigma p'_{ij}(u-\tau_{ijk})$ will be wide and with a low amplitude. This permits to determine easily the area where the impact was generated.

This computation is carried out for all the areas k with loop steps S204 and S205. At step S206, a characterizing value of each $P_k(u)$ is calculated and all the characterizing values noted $f(P_k(u))$ are compared. This characterizing value may be:

a maximal value of $P_k(u)$;
a power of $P_k(u)$, or a maximal square amplitude;
a maximal peak-to-peak amplitude;
a root mean square of $P_k(u)$;
an energy of $P_k(u)$, which equals $$\int_{u_{min}}^{u_{max}} P_k^2(u) \cdot du;$$

a width pulse parameter of $P_k(u)$, which equals $$\int_0^{w_{max}} \text{REAL}\left(\int_{u_i}^{u_{max}} P_k(u)e^{juw} \cdot du\right),$$

where REAL (x) is the real part of the complex number x.

Then, area $k_0$ corresponds to the area having the greatest characterizing value $f(P_{k_0}(u))$. Then, at step S207, the greatest value may be compared with a threshold of confidence, insuring that the detected impact was in the area $k_0$. Indeed, the impact could be an interference, due to noise, or due to an impact generated in another area than the M determined areas. Then, this last test permits to avoid undesired actions controlled by this device.

Moreover, this test may be replaced or combined with a test of contrast defined by the ratio $f(P_{k_0}(u))/\text{MEAN}(f(P_{k,k \neq k_0}(u)))$, where MEAN is an averaging operator of all the $f(P_k(u))$ values excluding that for $k=k_0$. If the contrast value is greater than a predetermined threshold, the result is considered as valid. Then, if the characterizing value of the area $k_0$ is considered as valid, it is considered that the impact occurred in this area. An action may be then driven by the device 3, for instance if this device is used as an interface. Else, this impact may be ignored by the device.

Moreover, it is possible to fit the results with an interpolation function as a sine $$X = \frac{\sin(x)}{x},$$

allowing to improve the resolution of this method.

This embodiment provides then a method for determining the location of impacts on a surface without an accurate synchronization, especially for non dispersive material.

However, in the case of dispersive material, a second embodiment is provided by the invention. The main difference in this embodiment is that the inverse Fourier transform of step S201 is a dispersion compensate Fourier transform. Indeed, a dispersive material is a material in which an acoustic signal propagation velocity depends on the frequency of the signal. In consequence, the waveform of a sensed signal propagated in this material is different from the original signal waveform. In this case, the dispersion compensate Fourier transform, as explained below, has to compensate the deformation of the signal due to propagation.

According to the proceeding of the Review of Progress in Quantitative Non-Destructive Evaluation entitled "A signal processing technique to remove the effect of dispersion from guided wave signals" from P. D. Wilcox & al, it is possible to determine the distance of the source a sensed acoustic signal with help of the following formula:

$$h(x) = \int_{-\infty}^{+\infty} G(\omega) \cdot e^{jk(\omega)x} \cdot d\omega,$$

where $G(\omega)$ is the Fourier transform of the sensed acoustic signal, and $k(\omega)$ is a wavenumber according to the relation dispersion. If it is considered that $k(\omega)=\Omega$ and that $\omega=m(\Omega)$, it is obtained from this formula:

$$h(x) = \int_{-\infty}^{+\infty} G(m(\Omega)) \cdot \frac{dm(\Omega)}{d\Omega} e^{j\Omega x} \cdot d\Omega,$$

which is the inverse Fourier transform of $$G(m(\Omega)) \cdot \frac{dm(\Omega)}{d\Omega}.$$

The shape of the signal obtained is modified, but the delay information remains the same because $$\frac{dm(\Omega)}{d\Omega}$$

is generally purely real. Then, this dispersion compensate inverse Fourier transform may be used for improving the first embodiment, providing thus a method for determining an impact on a dispersive material object surface.

Consequently, the method according to the second embodiment is substantially the same, except that, at step S201, the computed inverse Fourier transforms equal $$p'_{ij}(u) = \int_{-\infty}^{+\infty} P_{ij}(m(\Omega)) \cdot \left(\frac{dm(\Omega)}{d\Omega}\right)^2 \cdot e^{j\Omega u} \cdot d\Omega.$$

Then, this Fourier transform permits to compensate the dispersion of the signal, providing thus signals which may be processed.

In this embodiment, at step S203 the $\tau_{ijk}$ values are length based on the difference between the distance from the area k to the sensor i and the distance from the area k to the sensor j. The rest of the method remains unchanged.

In most of the cases, it can be considered that the waves generated by an impact on a substantially plane object are Lamb waves. As the waves in this embodiment of the invention are studied at low frequencies, we can consider that these waves are mainly zero order Lamb waves. Eventually, as the impact is generated on the surface, the waves generated are asymmetrical zero order Lamb waves. In consequence, at low frequencies, the dispersion relation substantially equals $\Omega = \alpha \sqrt{\omega}$ for instance, where $\alpha$ is a coefficient dependant on the material.

Then, it is possible to use the method of acoustic image with dispersive material for determining the location of impacts on a surface. The method of this second embodiment may also be applicable to non dispersive material, when it is used with the following dispersion relation: $\Omega = \alpha\omega$. Consequently, this embodiment provides a general method which is applicable to any kind of dispersive or non dispersive material. Indeed, it is easy to interpolate a dispersion relation of the propagated waves for every range of frequencies. The range of frequencies depends on the material, the application, and on the bandwidth of the sensors. This embodiment is then not limited to the current example of asymmetrical zero order Lamb waves.

Moreover, this coefficient $\alpha$ may also depend on the temperature of the material and this parameter may be taken into account. For instance, a temperature sensor may be fixed in the object, the coefficient $\alpha$ may be varied on the basis of this coefficient. In consequence, it is possible to provide a method which takes into account the temperature of the material. Similarly, if the material is anisotropic, i.e. the propagation velocity depends on the direction of propagation of the signal, this can be compensated by a coefficient $\alpha$ which depends on the path between a sensor i and an area k. For example, $\alpha$ depends on $\theta_{ik}$, where $\theta_{ik}$ is a determined angular value based on the respective locations of the area k and the sensor i.

According to the flowchart of FIG. 3, the method begins for example with an initializing mode which is illustrated by the flowchart of FIG. 5. During this initializing mode, the exact locations of the sensors may be input and stored in the device 3 S300, but these locations may also be input during the design of the device.

Thereafter, the dispersion relation is determined. Usually, the form of the dispersion relation is known. This step aims to provide the correct coefficient for interpolating this dispersion relation. In the case of asymmetrical zero order Lamb waves, we have to determine the coefficient $\alpha$. Yet, if the signals are studied in another range of frequencies, a polynomial interpolation of the dispersion relation may be required. Then, all the polynomial coefficients may have to be determined.

Furthermore, even if the material is considered as a non dispersive material, this step may be used to determine the correct coefficient $\alpha$, corresponding to this non dispersive material. To achieve the determining of the coefficient $\alpha$, NSO impacts may be generated on the surface of the material (S301 to S305) and the delays $\tau_{ijm}$ corresponding to each impact m are computed and stored in a memory. In an embodiment, the impacts are generated along a line linking two sensors, and are equally spaced. This permits to find easily the optimal value $\alpha$ coefficient.

Then, $\alpha$ test values will be tested on a determined range $[\alpha_{min};\alpha_{max}]$ from step S306 to step S314. The test values $\alpha$ are for example equally spaced of an increment $\Delta\alpha$ (S313). For each test value, the intercorrelation products $p'_{ijm}(u)$ corresponding to the impact m and to the sensors i and j, are computed with this test value $\alpha$ (S308) and summed (S309) for forming the $$P_m(u) = \sum_{i,j} p'_{ijm}(u - \tau_{ijm}).$$

Then, the $P_m(u)$ of all the impacts are summed, and the maximal value of this sum is stored in step S312. Thus, for each test value $\alpha$, a maximum $F(\alpha)$ is stored.

Then, at step S315, the greatest maximum, $\max(F(\alpha))$ is considered as the best value, so the corresponding $\alpha$ is chosen as the optimal coefficient $\alpha_{opt}$ and will be used during the operation of the device. Furthermore, a dichotomy method alone or combined with the last method could be used for searching the optimal coefficient.

Consequently, it is possible to provide a method of determining the location of impacts on a surface with efficient material dispersion compensation and based on acoustic imaging.

According to another embodiment, the initializing mode comprises a step of determining the locations and the corresponding delays of the M areas. For example, an operator may have to generate impacts on each sensitive area, and the device stores the corresponding delays in its ROM 5.

The invention claimed is:

1. A computer-implemented method that is tied to a particular tangible physical object that includes a surface having N acoustic sensors, where N is at least 3, and M determined areas, said computer-implemented method being for the determination of a location of an impact on said surface, said impact generating an acoustic signal, wherein each acoustic sensor receives said acoustic signal and transmits a sensed signal to a processing unit, said method comprising
   (a) computing P intercorrelation products $P_{ij}(\omega) = S_i(\omega) \cdot S^*_j(\omega)$, where $S_i(\omega)$ is a Fourier transform of a sensed signal $s_i(t)$ sensed by a sensor i of the N acoustic sensors; $Sj(\omega)$ is a Fourier transform of a sensed signal $sj(t)$ sensed by a sensor j of the N acoustic sensors; and "*" is the complex conjugate operator, whereby the Fourier transform of the sensed signals is given respectively by $S_i(\omega) = C_i(\omega) \cdot \exp(-j \times d_i) \cdot E(\omega)$, and $S_j(\omega) = C_j(\omega) \cdot \exp(-j \times d_j) \cdot E(\omega)$, where $C_i(\omega)$ and $C_j(\omega)$ are respective frequency complex responses of the sensors i and j, $x = \omega/C$ with C being an acoustic propagation velocity, $d_i$ and $d_j$ are respective distances between the impact location and the sensors i and j, and $E(\omega)$ is the Fourier transform of the impact waveform such that $P_{ij(\omega)}$ does not depend crucially on time origin and impact waveform;

(b) calculating P inverse Fourier transforms $p'_{ij}(u)$ of said $P_{ij}(\omega)$;

(c) computing, for each area k of the M determined areas, $P_k(u)=\Sigma p'_{ij}(u-\tau_{ijk})$, where in a non-dispersive surface, u is a time and $t_{ijk}$ is a stored predetermined delay value based on a difference between the respective locations of the area k and the sensors i and j, and in a dispersive surface, u is a distance and $t_{ijk}$ is a length depending on a distance between the area k and the sensor i and the distance between the area k and the sensor j; and (d) calculating a characterizing value $f(P_k(u))$ of each $P_k(u)$, and identifying, as the determined location of the impact, an area $k_0$ corresponding to an area k having a greatest characterizing value such that the function $P_{k0}(u)$ is closest to being an impulse.

2. The method as claimed in claim 1, wherein the inverse Fourier transforms $P'_{ij}(u)$ equal $$p'_{ij}(u) = \int_{-\infty}^{+\infty} P_{ij}(m(\Omega)) \cdot \left(\frac{dm(\Omega)}{d\Omega}\right)^2 \cdot e^{j\Omega u} \cdot d\Omega$$

where $\Omega$ is a wavenumber coefficient; and where $m(\Omega)$ is a frequency corresponding to the wavenumber coefficient $\Omega$, according to a material dispersion relation.

3. The method as set forth in claim 2, wherein the material dispersion relation substantially equals $\Omega=\alpha\sqrt{\omega}$, where $\alpha$ is a coefficient depending on the object.

4. The method as set forth in claim 2, wherein the material dispersion relation substantially equals $\Omega=\alpha\omega$, where $\alpha$ is a coefficient depending on the object.

5. The method as set forth in claim 3, wherein the coefficient $\alpha$ depends on $\theta_{ik}$, where $\theta_{ik}$ is a determined angular value based on the respective locations of the area k and the sensor i.

6. The method as set forth in claim 3, wherein the coefficient $\alpha$ depends on the temperature of the object $\alpha(T)$, where T is a temperature value.

7. The method as set forth in claim 2, further comprising an initializing mode comprising a step of determining the material dispersion relation of the object.

8. The method as set forth in claim 7, wherein said step of determining the material dispersion relation includes the following sub-step of generating NSO impacts at determined locations.

9. The method as set forth in claim 8, wherein said NSO impacts are generated at determined locations along a line linking two of the N sensors and equally spaced.

10. The method as set forth in claim 8, wherein the step of determining the material dispersion relation further comprises the following sub-steps:

computing $p'_{ij}(u)$ with $\alpha$ test values;

for each $\alpha$ test value, computing $P_m(u)=\Sigma p'_{ij}(u-\tau_{ijm})$ for each impact m, and for each $\alpha$ test value, summing all the $P_m(u)$; and selecting $\alpha_{opt}$ which provides the greatest maximal value of the sums $\Sigma P_m(u)$.

11. The method as set forth in claim 1 further comprising an initializing mode comprising a step of determining the location of the N sensors on the surface.

12. The method as set forth in claim 1, wherein the characterizing value of $P_k(u)$ is one of the following parameters:

a maximal value of $P_k(u)$;

a power of $P_k(u)$, or maximal square amplitude;

a maximal peak-to-peak amplitude;

a root mean square of $P_k(u)$; or an energy of $P_k(u)$, which equals $$\int_{u_{min}}^{u_{max}} P_k^2(u) \cdot du,$$

and a width pulse parameter of $P_k(u)$, which equals $$\int_0^{w_{max}} \text{REAL}\left(\int_{u_{min}}^{u_{max}} P_k(u)e^{juw} \cdot du\right),$$

where REAL(x) is the real part of the complex number x.

13. The method as set forth in claim 1, wherein it is concluded that the impact occurred in the area $k_0$ only if the characterizing value of $P_{k0}(u)$ is greater than a predetermined threshold of confidence.

14. The method as set forth in claim 1, wherein it is concluded that the impact occurred in the area $k_0$ only if a contrast value defined by the ratio $f(P_{k0}(u))/\text{MEAN}(f(Pk_{k\neq k0}(u)))$ is greater than a predetermined threshold of confidence where MEAN is an averaging operator and wherein f is a function that returns a greatest characterizing value of an argument thereof.

15. The method as set forth in claim 1, wherein $P_{ij}(\omega)$ is normalized.

16. A device for determining the location of an impact on a surface of an object, said surface comprising M determined areas and said impact generating an acoustic signal, said device comprising: a processing unit; and N acoustic sensors adapted to be borne by said surface, where N is at least 3, each sensor i receiving said acoustic signal and transmitting a sensed signal $s_i(t)$ to the processing unit, wherein said processing unit comprises: means for computing P intercorrelation products $P_{ij}(\omega)=S_i(\omega)\cdot S^*_j(\omega)$, where $S_i(\omega)$ is a Fourier transform of a sensed signal $s_i(t)$ sensed by a sensor i of the N acoustic sensors; $Sj(\omega)$ is a Fourier transform of a sensed signal sj(t) sensed by a sensor j of the N acoustic sensors; and "*" is the complex conjugate operator, whereby the Fourier transform of the sensed signals is given respectively by $S_i(\omega)=C_i(\omega)\cdot\exp(-j\times d_i)\cdot E(\omega)$, and $S_j(\omega)=C_j(\omega)\cdot\exp(-j\times d_j)\cdot E(\omega)$, where $C_i(\omega)$ and $C_j(\omega)$ are respective frequency complex responses of the sensors i and j, $x=\omega/C$ with C being an acoustic propagation velocity, $d_i$ and $d_j$ are respective distances between the impact location and the sensors i and j, and $E(\omega)$ is the Fourier transform of the impact waveform such that $P_{ij}(\omega)$ does not depend crucially on time origin and impact waveform; means for calculating P inverse Fourier transforms $p'_{ij}(u)$ of said $p'_{ij}(\omega)$; means for computing, for each area k of the M determined areas, $P_k(u)=\Sigma p'_{ij}(u-\tau_{ijk})$, where in a non-dispersive surface, u is a time and $t_{ijk}$ is a stored predetermined delay value based on a difference between respective locations of the area k and the sensors i and j, and in a dispersive surface, u is a distance and $t_{ijk}$ is a length depending on a distance between the area k and the sensor i and the distance between the area k and the sensor j; and means for calculating a characterizing value $f(P_k(u))$ of each $P_k(u)$, and identifying, as the determined location of the impact, an area $k_0$ corresponding to an area k having a greatest characterizing value such that the function $P_{k0}(u)$ is closest to being an impulse.

17. The method of claim 1, wherein identifying an area index $k_0$ for which the function $P_{k0}(u)$ is closest to being an impulse comprises finding $k_0$, wherein a characterizing value of $P_{k0}(u)$ is greater than corresponding characterizing values of $P_k(u)$ for $k\neq k_0$.

18. The device of claim 16, wherein the means for identifying an area index $k_0$ for which the $P_{k0}(u)$ is closest to being an impulse comprises means for determining $k_0$, where a characterizing value of $P_{k0}(u)$ is greater than corresponding characterizing values of $P_k(u)$ for $k \neq k_0$.

* * * * *

UNITED STATES PATENT AND TRADEMARK OFFICE
CERTIFICATE OF CORRECTION

PATENT NO.       : 8,692,810 B2
APPLICATION NO.  : 11/911398
DATED            : April 8, 2014
INVENTOR(S)      : Ing It is certified that error appears in the above-identified patent and that said Letters Patent is hereby corrected as shown below:

In the claims:

Column 10,
Line 42, "$S_l(\omega)$" should read --$S_i(\omega)$--.

Signed and Sealed this
Fifteenth Day of July, 2014

Michelle K. Lee
*Deputy Director of the United States Patent and Trademark Office*